United States Patent [19]

Graham et al.

[11] Patent Number: 5,439,966

[45] Date of Patent: Aug. 8, 1995

[54] POLYETHYLENE OXIDE TEMPERATURE - OR FLUID-SENSITIVE SHAPE MEMORY DEVICE

[75] Inventors: Neil B. Graham, Bearsden; Marion E. McNeill, Milngavie, both of Scotland

[73] Assignee: National Research Development Corporation, London, United Kingdom

[21] Appl. No.: 1,414

[22] Filed: Jan. 7, 1993

Related U.S. Application Data

[63] Continuation of Ser. No. 865,658, Apr. 7, 1992, abandoned, which is a continuation of Ser. No. 678,196, Apr. 1, 1991, abandoned, which is a continuation of Ser. No. 275,624, Nov. 15, 1988, abandoned, which is a continuation of Ser. No. 841,526, Mar. 12, 1986, abandoned filed as PCT/GB85/00313, Jul. 12, 1985.

[30] Foreign Application Priority Data

Jul. 12, 1984 [GB] United Kingdom ............... 8417810

[51] Int. Cl.$^6$ ............................................. C08J 5/00
[52] U.S. Cl. ........................ 528/421; 514/772.1; 514/772.3; 528/425; 528/502 B; 264/230; 264/342 R

[58] Field of Search ............... 424/78.1, 422; 514/772.1, 772.3; 526/320, 323.1, 322; 528/403, 421, 481, 502, 425; 264/230, 291, 342, 342 RE, 346, 348

[56] References Cited

U.S. PATENT DOCUMENTS

| | | | |
|---|---|---|---|
| 3,377,261 | 4/1964 | Ancker et al. | 204/159.1 X |
| 3,547,792 | 12/1970 | Patterson | 204/159.14 |
| 3,875,284 | 4/1975 | Sasaguri et al. | 264/288 |
| 4,296,227 | 10/1981 | Seeburger et al. | 520/320 |
| 4,542,176 | 9/1985 | Graham | 524/543 |
| 4,691,045 | 9/1987 | Fuekuchi et al. | 526/320 |
| 4,931,288 | 6/1990 | Embrey et al. | 424/422 |

FOREIGN PATENT DOCUMENTS

| | | |
|---|---|---|
| 55-10624 | 8/1980 | Japan . |
| 1566552 | 5/1980 | United Kingdom . |
| 0067671 | 12/1982 | United Kingdom . |

*Primary Examiner*—Thurman K. Page
*Assistant Examiner*—Peter F. Kulkosky
*Attorney, Agent, or Firm*—Oblon, Spivak, McClelland, Maier & Neustadt

[57] ABSTRACT

A temperature- and/or polar fluid-sensitive device which comprises a mechanically strained semi-crystalline hydrophilic polymer.

5 Claims, No Drawings

POLYETHYLENE OXIDE TEMPERATURE - OR FLUID-SENSITIVE SHAPE MEMORY DEVICE

This application is a continuation Ser. No. 07/865,658 filed Apr. 7, 1992, now abandoned. Which is a continuation of Ser. No. 07/678,196 filed Apr. 1, 1991 now abandoned which is a continuation of Ser. No. 07/275,624 filed Nov. 15, 1988 now abandoned which is a continuation of Ser. No. 06/841,526 filed Mar. 12, 1986 now abandoned, which was filed as International Application No. PCT/GB85/00313 on Jul. 12, 1985.

This invention relates to temperature- or fluid-sensitive devices; more particularly, this invention relates to polymeric devices which are sensitive to temperature and/or polar fluids; and processes for their preparation; and to methods of using them.

There are many sectors of industry where it would be highly desirable to provide a device for detecting whether a locus (for example, a perishable or sterile article) has been subjected to a change in temperature and/or to contact with a polar fluid; examples include the food packaging industry and the health care product industry.

The invention seeks to provide such a device. In accordance with other embodiments, hereinafter described, this invention also seeks to provide alarm systems; fluid-flow controlling devices; controlled release dosage forms for active substances; and plugs for human or animal body orifices which also release active substance.

According to this invention, there is provided a temperature- and/or polar fluid-sensitive device which comprises a mechanically strained semi-crystalline hydrophilic polymer.

It is desirable that the hydrophilic polymer is chemically crosslinked so that, on activation of the device by a change in temperature and/or contact with a polar fluid, the stress restoring the device to a mechanically unstrained state is maximised. Chemical crosslinking may be effected in a manner known per se. Where the hydrophilic polymer comprises functional groups which comprise an active hydrogen atom (for example: hydroxyl; amino, mercapto; carboxylic or phosphoric acid, amide or thiolic or thionic analogues) chemical crosslinking may be effected by means of di- or poly-isocyanate (such as bis-4-isocyanatophenyl)methane) or a di- or poly- linear or cyclic olefinically unsaturated ether (such as acrolein tetramer); for example, as disclosed in our GB 20470093B, GB 2047094B and GB 2108517B, from which it will be apparent that where a diisocyanate or di-olefinically unsaturated ether is used a reactant comprising at least three active hydrogen atoms must also be present to ensure chemical crosslinking.

In general, a lower amount of crosslinking the mechanical straining process of the invention; thus, where polyethylene oxide is the hydrophilic polymer crosslinked through a triol, such as hexanetriol, it is found preferable to use no more than 4 and desirably from 0.5 to 2 moles of the triol per mole of the polyethylene oxide.

Entanglement crosslinking may be utilised, especially where the hydrophilic polymer has a high (for example, $\overline{M}_n$ greater than 20,000) molecular weight, by chemically crosslinking, in intimate admixture with the hydrophilic polymer, at least one monomer of functionality greater than two. Examples of such monomers include di- and poly- olefinically unsaturated hydrocarbons, such as divinyl benzene or isoprene, and di- and polyolefinically unsaturated esters or ethers, such as acrolein tetramer, triallyl cyanurate or glycol dimethacrylate. (Such chemical crosslinking differs from the physical entanglements found in high molecular weight polymers and results in a type of interpenetrating polymer network.)

It is a preferred feature of this invention that the hydrophilic polymer comprises polyethylene oxide residues, especially wherein the number average molecular weight, $\overline{M}_n$, of the polyethylene oxide is greater than 1,500, preferably greater than 3,000; for example, from 4,000 to 12,000 or higher. Such polyethylene oxide is particularly suited to use in accordance with this invention: thus, it exhibits a significant (typically greater than 5% by weight) degree of crystallinity; it has a crystallite melting temperature, Tm, which may readily be varied in the opposite range from about $-10°$ C. to $+70°$ C., and it readily absorbs polar fluids, especially at ambient temperatures, with concomitant dissolution of the crystallites and restoration of the device to a mechanically unstrained state.

The polar fluid may be in the liquid phase but the devices of this invention are also sensitive to polar fluids in the vapour phase, especially at elevated temperature. Examples of polar fluids to which the devices of this invention are sensitive include water (both as liquid and steam); lower alkanols, such as methanol and ethanol; lower amides, such as dimethylformamide; and chloroform.

The hydrophilic polymer may be a homopolymer or a random, alternating or block copolymer. In the specific case of an ethylene oxide polymer this may be a homopolymer or a random or block copolymer of ethylene oxide with, for example, a homologue such as propylene oxide or oxetane.

Up to 30% by weight of the polyethylene oxide may be replaced by a higher homologue, for example polypropylene oxide or polybutylene oxide. Also, the polyethylene oxide may contain up to 30% by weight of species having a $\overline{M}n$ less than 1,500; for example 1,000 or less. The hydrophilic polymer, for example, polyethylene oxide, may also be foamed in a manner known per se. For example, the polyethylene oxide may be chemically crosslinked by means of a di- or poly-isocyanate in the presence of water; the polyethylene oxide may also be foamed by the direct injection of a pneumatogen, such as a freon; for example, fluorotrichloromethane (e.g. "ARCTON" ex ICI Ltd: "ARCTON" is a registered Trademark).

The device according to this invention may comprise a hydrophilic polymer as herein defined which is formed as a film, a slab, a sheet, a hollow profile, such as a cylinder, or a rod, or a combination thereof. The device may also comprise one or more holes or hollows.

It is a further preferred feature of this invention that the hydrophilic polymer has been mechanically strained to a deformation ratio from 1.1 to 10, preferably 2 to 8; for example, from 4 to 6. By "deformation ratio" is meant herein the ratio of the final length of the sample of hydrophilic polymer after mechanical straining to the initial length of the sample before mechanical straining. (For a sample of uniform cross-sectional area and undergoing a negligible change in volume in deformation this is also the ratio of the initial cross-sectional area of the sample to the final cross-sectional area.)

In accordance with a further aspect of this invention, there is provided a process for the preparation of a temperature- and/or polar fluid-sensitive device which comprises:
(i) subjecting a semi-crystalline hydrophilic polymer to a deforming stress so that the hydrophilic polymer is mechanically strained; and
(ii) where the deformation was effected at or above Tm, cooling the mechanically strained hydrophilic polymer to a temperature below Tm while maintaining the deforming stress.

Preferably the hydrophilic polymer is as herein defined.

It is found, in accordance with this invention in its broadest aspect, that a semi-crystalline hydrophilic polymer in which a significant degree of crystallinity exists exhibits a useful "memory" after cold deformation (that is, where (i) above is effected below Tm) or hot deformation (that is, where (i) is effected above Tm) followed by (ii). The memory is activated by destroying the crystallites by heating above Tm; or by contact with polar fluid; or, indeed, both (for example, by contact with steam). When this is done the polymer reverts to essentially its original mechanically unstrained shape (although imbibing polar fluid will increase the dimensions of the polymer).

In accordance with a preferred aspect of this invention, there is provided a process as aforesaid wherein, in (i), the semi-crystalline hydrophilic polymer is at a temperature above Tm. In hot deformation not only can greater deformation ratios, for example from 5 to 12, be obtained but also there is a lower incidence of mechanical failure.

The deforming stress used in the process of this invention may be tensile, compressive or shear (or the deformation may be more a complex mode involving at least two of these); it is preferred, however, that the deforming stress is a tensile stress. Such a situation obtains in a reactive melt extrusion production line involving drawing between rolls rotating at different surface linear speeds. It also obtains where the hydrophilic polymer is deformed by passage in the solid phase through a reducing die; for example, die drawing or draw-assisted hydrostatic extrusion.

Slab, sheet, hollow profiles such as a cylinder, or rod extended uniaxially in the machine direction will, on activation by the elastic energy of the hydrophilic polymer, contract in length along the machine direction with concomitant expansion in the other directions.

Such forms, especially hollow profiles such as a cylinder, may, however, be extended biaxially by being subjected to a hoop stress transverse to the machine direction by one or more of the following means, namely by the internal application of compressed fluid (or external application of a vacuum), preferably above Tin, or by being extruded and/or drawn over a mandrel of the same profile as, but larger dimensions than, the internal hollow profile. These forms will, on activation by the elastic energy of the hydrophilic polymer, expand in length along the machine direction with concomitant contraction in other directions.

If, instead of extension, compression is the deformation which is effected the opposite effect, on activation by the elastic energy of the hydrophilic polymer, will be observed.

This invention also provides a temperature- and/or polar fluid-sensitive device whenever so prepared.

According to a further aspect of this invention, there is provided an alarm system which comprises a device as hereinbefore described and, activatable by any elastic energy released by the hydrophilic polymer should it revert to essentially its original mechanically unstrained state by reason of its being subject to unacceptible temperature (above Tin) and/or polar fluid (herein referred to as "activation by the elastic energy of the hydrophilic polymer"), warning means.

In one embodiment of this aspect of the invention the system comprises as passive warning means, one or more indicia (for example, the words "FAILED" or "CONTAMINATED" positioned on heat- or water-sensitive goods such as instrumentation, sterile health care products or perishable materials such as foodstuffs which may be frozen foodstuffs) which, under normal circumstances, will be concealed by the device comprising the hydrophilic polymer; for example, in the form of a slab or sheet. On activation by the elastic energy of the hydrophilic polymer the device deforms and exposes the indicia. In another embodiment of this aspect of the invention the system comprises, as active warning means, one or more audible and/or visible warning means which, in normal circumstances, remain inactive. On activation by the elastic energy of the hydrophilic polymer the device deforms to actuate, for example via microswitching means or a piezoelectric pressure transducer (especially where the hydrophilic polymer is of hollow profile) an audible alarm such as a bell or hooter and/or a visible alarm such as continuously or intermittently illuminated indicia. The device may also comprise a hydrophilic polymer which is dyed or otherwise opacified thereby concealing a light source and which, on activation by the elastic energy of the hydrophilic polymer, deforms to expose the light source thereby permitting the light to actuate a photoelectric cell-controlled alarm.

According to another aspect of this invention, there is provided a polar fluid flow-controlling device which comprises an elongate member of a device as aforesaid and dimensioned as an internal or external sleeve or as a plug for a polar fluid conduit and which, on activation by the elastic energy of the hydrophilic polymer, deforms to provide a fluid-tight fit to the conduit. The elongate member may be a hollow profile which, when biaxially extended or compressed, or uniaxially compressed or extended, as aforesaid, can be used as an external or internal sleeve, respectively, for the polar fluid conduit, for example at a leak or a joint, whether these are pipes conveying water (or other polar fluids) or, as a tourniquet, for plant or animal vascular systems. In particular, this invention provides a polar fluid flow-controlling device as aforesaid for use in surgery; for example, as a tourniquet or catheter. The elongate member may be a rod which, when uniaxially extended or biaxially compressed as aforesaid, can be used as a plug as aforesaid. In all cases, on activation by the elastic energy of the hydrophilic polymer the device deforms to provide a fluid-tight fit to the conduit.

In accordance with a further, and preferred, aspect of this invention there is provided a controlled release dosage form which comprises a device as aforesaid and at least one active substance, preferably wherein the, or at least one of the, active substances comprises a drug, though the active substance may be any of the active substances disclosed in our aforementioned applications.

Such a controlled release dosage form may suitably comprise a device as herein described formed as a slab, a sheet, a rod or a hollow profile; for example, a cylinder or a ring.

One particular example of a dosage form is prepared by winding a pre-heated silicone or polyethylene tube of appropriate dimensions about a cylindrical or toroidal mandrel; incorporating the hydrophilic polymer or the reactant mixture therefor in the tubing mould so formed; allowing the mixture to cure, if required; cooling the semicrystalline hydrophilic polymer; stripping it from the tubing; heating the hydrophilic polymer above $T_m$ and deforming it at that temperature, for example to a uniaxially extended rod; and cooling the uniaxially extended rod below $T_m$. It is particularly preferred that the hydrophilic polymer comprises polyethylene oxide, especially a hydrolysable hydrophilic such polymer; for example wherein the polyethylene oxide has been cross-linked by reaction with a di- or poly-linear or cyclic olefinically unsaturated ether. Where such hollow profiles are uniaxially extended, or biaxially compressed as aforesaid (the rings being formed by slicing, below Tm, a hollow cylinder into bands), they expand on contact with a polar fluid. With such controlled release dosage forms it is possible to get controlled, sustained release of active substance occurring in the stomach. (It may be convenient to administer such dosage forms placed in a hard gelatin capsule). Thus the initially dry dosage form rapidly expands in the gastric juice (and also, if the hydrophilic polymer Tm is less than 37° C., by reason of the enhanced temperature) until it cannot pass through the duodenal sphincter until polymer degradation occurs, a period which can, as disclosed in our aforementioned applications, by design, be varied from days to months. As mentioned previously, the hydrophilic polymer may be foamed; it is found that the expansion is much greater for foams, preferably open celled foams.

It is preferred that the active substance is incorporated into the device as aforementioned; it is, however, possible (for example, in the aforementioned gastric prophylaxis or therapy) simply to utilise the device as a retaining means for a different active substance releasing mechanism attached thereto.

In accordance with a further embodiment of this aspect of the invention, there is provided a composite controlled release dosage form as aforesaid which further comprises at least one other hydrophilic polymeric member in co-operating relationship with a device as aforesaid. Preferably, the device as aforesaid comprises either a hollow profile such as a cylinder or a core which co-operates with a core or a hollow profile such as a cylinder, respectively, of the, or at least one of the, other hydrophilic polymeric members. Cores may themselves be co-operating hollow profiles. The, or at least one of the, other hydrophilic polymeric members may be a device of this invention which may have the same or different composition and/or Tm and/or degree of swelling in a given polar fluid. An active substance need only be incorporated in one polymeric component (the term "component" is used to include all devices and other polymeric members in a composite controlled release dosage form) of this embodiment of the invention. An active substance or a mixture of active substances may, however, be incorporated in a plurality of components. The same or different active substance, or mixture of active substances, may be used in each such component. Where the same active substance, or mixture of active substances, is used in a plurality of components, the concentration thereof in each component may be the same or different.

In accordance with a particularly preferred example of this embodiment of the invention, there is provided a composite controlled release dosage form which comprises a hollow, preferably cylindrical, sleeve co-operating with a core at least one of which, and possibly both, comprises a device as aforesaid and at least one of which (not necessary the device as aforesaid), and possibly both, has an active substance incorporated therein. If the core is a device as aforesaid it is preferably uniaxially extended or biaxially compressed; if the sleeve is a device as aforesaid it is preferably biaxially extended or uniaxially compressed. The result of this is that, on activation by the elastic energy of the hydrophilic polymer (for example, by contact with patient body fluids on administration), the sleeve and core are urged into tighter co-operation.

All of the aforementioned controlled release dosage forms exhibit valuable active substance release profiles.

In a modification of the last-mentioned embodiment, this invention provides a method of forming a tight fit between a device as aforesaid and another polymer material which may be a hydrophilic polymer, for example, a device according to this invention. The method comprises positioning co-operating profiles of the components; and heating the assembly of components above the Tm of the or each component device of the invention thereby shrink or expansion (depending on whether the device is uniaxially or biaxially extended or compressed as aforesaid) fitting the components into tighter co-operation. One, or a plurality, of the components may comprise an active substance, or a mixture of active substances, incorporated therein as aforesaid. One profile may be that of a reservoir dosage form while the other is a mating plug therefor. The plug may be mated with a plurality of such reservoirs, for example to provide a rectal pessary or oral dosage form.

In accordance with a still further aspect of this invention, there is provided a plug for a human or animal body orifice which comprises a device as aforesaid and, optionally, an active substance. The plug may be formed as a helical rod as aforesaid or as a dumb-bell shape and mechanically strained to a substantially linear configuration in accordance with the process of this invention prior to insertion in the body orifice. Thus orifice may comprise a duct, for example, a tear duct or a teat duct in cattle, or a body cavity, for example a uterine cervix. The plug may comprise a drug, for example an antibiotic, and by insertion into a teat duct, for example as a mechanically strained helical rod, may be used for prophylaxis or therapy of mastitis during the drying out period of cattle. The plug may, however, be used without active substance and by insertion into a uterine cervix, for example as a mechanically strained dumb-bell form, may be utilised for gentle dilation prior to examination or abortion. In the latter case it may comprise an abortifacient.

Both the body fluid and, if the hydrophilic polymer $T_m$ is less than 37° C., the body temperature cause the inserted plug to return to its mechanically unstrained shape (for example, a helical rod or dumb-bell) thereby facilitating the retention of the plug.

It is particularly preferred that the hydrophilic polymer comprises a hydrolysable hydrophilic polymer.

The following Examples illustrate the invention.

EXAMPLE 1

The invention shown in Table 1 were thoroughly mixed and heated together, with ferric chloride as catalyst in an amount of 7 mg g$^{-1}$ total polymer-forming reactants, at 95° C. for 4 hours. The melt was then, in each case except the last set cast to form a 0.95 mm film of chemically crosslinked polyethylene oxide (PEO) hydrogel as characterised in Table 1. (The films formed from PEO 8400 were made by casting a block of polymer; and then skiving films therefrom.)

TABLE 1

| Reactant composition | wt % Crystalinity in polymeric product | |
|---|---|---|
| | Based on total polymers | Based on PEO content |
| PEO 4360[1] + 1 HT[2] | 36.8 | 43.4 |
| PEO 4360[1] + 2 HT[2] | 24.7 | 31.5 |
| PEO 4360[1] + 3 HT[2] | 16.4 | 23.4 |
| PEO 4360[1] + 5 HT[2] | 7.0 | 11.0 |
| PEO 4360[1] + 7 HT[2] | 6.0 | 11.4 |
| PEO 4360[1] + 9 HT[2] | N.D. | N.D. |
| PEO 5830[3] + 1 HT[2] | 34.2 | 38.3 |
| PEO 5830[3] + 3 HT[2] | 24.8 | 31.9 |
| PEO 5830[3] + 4 HT[2] | N.D. | N.D. |
| PEO 5830[3] + 5 HT[2] | 21.5 | 31.2 |
| PEO 5830[3] + 7 HT[2] | 10.2 | 32.9 |
| PEO 5830[3] + 9 HT[2] | 15.2 | N.D. |
| PEO 8400[2] + 0.75 HT[2] | 50.3 | 54.3 |
| PEO 8400[2] + 1 HT[2] | 43.0 | 47.1 |
| PEO 8400[2] + 2 HT[2] | 31.7 | 36.8 |
| PEO 8400[2] + 4 HT[2] | 30.5 | 39.1 |
| PEO 8400[2] + 6 HT[2] | 25.4 | 35.9 |
| PEO 8400[2] + 8 HT[2] | 24.9. | 38.1 |

1,3,4 denote polyethylene oxides ("BREOX" ex BP Chemicals Ltd.) of average molecular weight of 4360, 5830 and 8400, respectively, as measured by ASTM D1638-66T.

[2] denotes the number of moles, relative to one mole of PEO, of hexane-1,2,6-triol (ex Aldrich Chemicals Ltd.) mixed with the PEO prior to mixing with stoichometric amount of 4,4'-dicyclohexylmethane diisocyanate ("DESMODUR W" ex Bayer).

N.D. denotes the value was not determined.

Strips of the cast film were then heated to a temperature above the crystallite melting point (for example, were heated to 45° C.); rolled at that temperature to give a cylindrical device of spiral cross-section; and cooled to a temperature below the crystallite melting point (for example, to ambient temperature).

Recovery of the original shape could be attained either by reheating the strips of the cast film above the crystallite melting point or by swelling (for example, in water or chloroform). Such a rolled device, incorporated into a hard gelatin capsule, forms the basis of a prolonged gastric retention oral dosage form.

This Example illustrates the preparation of plugs, formed as helical rods and mechanically strained to a substantially linear configuration, comprising a hydrolysable hydrophilic polymer and an antibiotic; the regain of the rods original configuration; and the release profile of the antibiotic from the plug.

Ferric chloride (ex BDH Ltd.) was added, as catalyst, to 1,2,6-hexane triol (ex Aldrich Chemicals Ltd.) dried at ambient temperature under vacuum for 36 hours, with stirring and slight heating until a homogeneous melt was obtained. Polyethylene oxide (PEO) of number average molecular weight $\overline{M}_n$ of 3330 ("BREOX" ex BP Chemicals Ltd. vacuum dried under nitrogen for 6 hours and stored under nitrogen until use) was then preheated to 95° C. and added to the melt until homogeneity was regained. Acrolein tetramer (triply distilled under vacuum and characterised by IR and proton NMR spectra, and refractive index) was next added and mixed at 95° C. until the mix was homogeneous. The respective amounts of the reactants are shown in Table 2.

The reactant mixture was placed in a syringe (pre-warmed to prevent premature crystallisation of the PEO) and degassed. The degassed mixture was thereafter injected into a pre-warmed length of clean silicone tubing (2 mm I.D; 1 mm wall thickness) helically formed around a tubular mandrel of 35 mm diameter; the tubing ends were sealed; and the entire tubing mould assembly was placed in an oven at 95° C. to cure for 4 hours. After curing, the mould was cooled to below 30° C. and then the silicon tubing was cut and stripped from the hydrogel which was next cut into 115 mm long sections, or loops.

TABLE 2

| Sample No. | PEO | | Hexane triol | | Acrolein tetramer | | Ferric chloride Weight |
|---|---|---|---|---|---|---|---|
| | Mol Rat | Weight (g) | Mol Rat | Weight (g) | Mol Rat | Weight (g) | |
| 1 | 1 | 5 | 1 | 0.202 | 4.816 | 1.62 | 0.0068 |
| 2 | 1 | 5 | 2 | 0.403 | 4.816 | 1.62 | 0.007 |
| 3 | 1 | 5 | 3 | 0.605 | 4.816 | 1.62 | 0.0072 |

Loops of Sample 2 were placed in a known volume of 60/40 v/v ethanol/methanol containing in solution a known weight of benzathine cloxacillin (ex Beechams, stored under dry conditions at 4° C.); and the mixture was sealed in a small polyethylene bag to prevent solvent evaporation. The loops were then allowed to swell fully, removed and dried in air at room temperature. Residual solvent was then removed under vacuum at room temperature to provide loops of hydrolysable hydrophilic polymer impregnated with benzathine cloxacillin.

The dried, antibiotic-loaded loops were then heated above the crystalline melting point but below 50° C.; held in tension; and cooled to a temperature below the crystalline melting point to provide rods of substantially linear configuration. The rods were thereafter individually placed in a Sorensent's buffer solution having a pH of 6.5 (corresponding to the pH of fresh cow's milk) at 37° C. The rods released the antibiotic into the buffer solution; UV absorption readings were made at regular intervals and from a calibration curve the amount of antibiotic released was determined. Results are given in Table 3. It was also visually observed that the rod, by reason of the dissolution of crystallites by aqueous media and by reason of the elevated temperature, reverted to its loop configuration. Separate parallel tests on unloaded rods indicated a loss in weight of some 50% of the original dry weight, due to hydrolysis and manifest by turbidity and flocs in the aqueous media, over 7 weeks.

TABLE 3

| Antibiotic released (mg) | Time (day 1) |
|---|---|
| 46 | 0.1 |
| 67 | 0.3 |
| 82 | 1.0 |
| 84 | 4.0 |
| 85 | 5.0 |
| 86 | 5.5 |

These in vitro studies strongly indicate that such plugs will be of use in the treament, either by prophylaxis or therapy, of bovine mastitis. Loaded rods are inserted into the teat duct where they commence releasing antibiotic and reverting to this original form (which assists in their retention). Thereafter they hydrolyse to dischargeable by-products thereby obviating the need for a second veterinary attendance.

We claim:

1. A device which changes its shape when its temperature is increased above a threshold level or when it has its surface contacted by a polar fluid, in which the device is made of a shaped body of material which comprises a chemically cross-linked, water-insoluble, hydrophilic polymer having polyethylene oxide units, said units having a number average molecular weight ($\overline{M}_n$) of from 1,500 to 12,000, which polymer has in it regions of crystalline material of which the crystallite melting temperature ($T_m$) lies in the range from $-10°$ C. to $70°$ C., and in which the body has been mechanically strained to a deformation ratio in the range of 1.1 to 10 prior to its being heated or exposed to a polar fluid, being retained in its strained shape solely by internal forces which may be reduced or removed to permit the device to resile towards its unstrained shape.

2. A device as claimed in claim 1, in which the device in the form of a shaped body of a hydrophilic polymer consists essentially of 70 to 100% of polyethylene oxide units, with the balance being polypropylene oxide or polybutylene oxide units.

3. A process for the preparation of a device which changes its shape when its temperature is increased above a threshold level or when it has its surface contacted by a polar fluid, which comprises the steps of:
   1) subjecting a shaped body of material which comprises a chemically cross-linked, water-insoluble, hydrophilic polymer having polyethylene oxide units, said units having a number average molecular weight ($\overline{M}_n$) of from 1500 to 12000, which polymer has in it regions of crystalline material of which the crystallite melting temperature ($T_m$) lies in the range of from $-10°$ C. to $+70°$ C., to a stress causing it to be mechanically strained to a deformation ratio in the range of 1.1 to 10;
   2) effecting the deformation at a temperature at or above $T_m$ and
   3) cooling the strained body to a temperature below $T_m$ while maintaining the deforming stress on it.

4. A process as claimed in claim 3, in which the deformation stress is tensile.

5. A process as claimed in claim 3, in which the deformation stress is a hoop stress.

* * * * *